United States Patent [19]

Gilroy

[11] Patent Number: 5,055,294
[45] Date of Patent: Oct. 8, 1991

[54] CHIMERIC *BACILLUS THURINGIENSIS* CRYSTAL PROTEIN GENE COMPRISING HD-73 AND BERLINER 1715 TOXIN GENES, TRANSFORMED AND EXPRESSED IN *PSEUDOMONAS FLUORESCENS*

[75] Inventor: Thomas E. Gilroy, San Diego, Calif.

[73] Assignee: Mycogen Corporation, San Diego, Calif.

[21] Appl. No.: 164,162

[22] Filed: Mar. 3, 1988

[51] Int. Cl.$^5$ .................. C12P 21/00; C07H 15/12; C12N 1/20; C12N 15/00

[52] U.S. Cl. .................. 424/93; 435/172.3; 435/252.3; 435/252.33; 435/255; 435/252.31; 435/252.34; 435/252.32; 435/254; 435/256; 435/320.1; 435/67.1; 435/69.7; 536/27; 932/64; 932/72

[58] Field of Search ............ 435/69.1, 172.3, 91, 435/320.1, 252.31, 252.34, 252.33, 252.32, 255, 240.2, 254, 256; 536/27; 935/22, 60, 65, 72, 74; 424/93

[56] References Cited

U.S. PATENT DOCUMENTS 4,448,885  5/1984  Schnepf et al. .................. 435/172.3
4,467,036  8/1984  Schnepf et al. .................. 435/172.3
4,771,131  9/1988  Herrnstadt et al. .................. 536/27

OTHER PUBLICATIONS

Schnepf, H. E., and Whitely, H. R. (1981) "Cloning and Expression of *Bacillus thuringiensis* Crystal Protein Gene in *Escherichia coli*," Proc. Natl. Acad. Sci. U.S.A. 78:2893-2897.

Geiser et al., *Gene*. vol. 48, 1986, pp. 109-118, "The Hypervariable Region in the Genes Coding for Entomopathogenic crystal proteins of *Bacillus thuringiensis*" . . . HD1.

Adong et al., *Gene* vol. 36, 1985, pp. 289-300 "Characterized Full-Length and Truncated Plasmid Clones of the Crystal Protein of *Bacillus thuringiensis*", Manduca sexta.

Wabiko et al., DNA vol. 5, pp. 305-314, 1986 "Bacillus thuringiensis Entomocidal Protoxin Gene Sequence and gene Product Analysis".

Primary Examiner—Robin L. Teskin
Attorney, Agent, or Firm—Saliwanchik & Saliwanchik

[57] ABSTRACT

A novel hybrid B.t. toxin gene toxic to lepidopteran insects has been cloned. The DNA encoding the B.t. toxin can be used to transform various prokaryotic and eukaryotic microbes to express the B.t. toxin. These recombinant microbes can be used to control lepidopteran insects in various environments.

28 Claims, 30 Drawing Sheets

Figure 1-1

```
ATG GAT AAC AAT CCG AAC ATC AAT GAA TGC ATT CCT TAT AAT TGT TTA   48
AGT AAC CCT GAA GTA TTA GGT GGA GAA AGA ATA GAA ACT GGT           96
TAC ACC CCA ATC GAT ATT TCC TTG TCG CTA ACG CAA TTT CTT TTG AGT  144
GAA TTT GTT CCC GGT GCT GGA TTT GTG TTA GGA CTA GTT GAT ATA ATA  192
TGG GGA ATT TTT GGT CCC TCT CAA TGG GAC GCA TTT CTT GTA CAA ATT  240
GAA CAG TTA ATT AAC CAA AGA GGA CTA GAA GAA TTC GCT AGG AAC CAA GCC  288
ATT TCT AGA TTA GAA CTA AGC AAT CTT TAT CAA ATT CCA GCA TTA TAC GCA GAA  336
TCT TTT AGA GAG TGG GAA GCA GAT CCT ACT AAT CCA GCA TTA AGA GAA  384
GAG ATG CGT ATT CAA TTC AAT GAC ATG AAC AGT GCC CTT ACA ACC GCT  432
ATT CCT CTT TTT GCA GTT CAA AAT TAT CAA GTT CCT CTT TTA TCA GTA  480
TAT GTT CAA GCT GCA AAT TTA CAT TTA TCA GTT TTG AGA GAT GTT TCA  528
```

Figure 1-2

```
GTG TTT GGA CAA AGG TGG GGA TTT GAT GCC GCG ACT ATC AAT AGT CGT   576
TAT AAT GAT TTA ACT AGG CTT ATT GGC AAC TAT ACA GAT TAT GCT GTA   624
CGC TGG TAC AAT ACG GGA TTA GAA CGT GTA TGG GGA CCG GAT TCT AGA   672
GAT TGG GTA AGG TAT CAA TTT AGA AGA GAA TTA ACA CTA ACT GTA       720
TTA GAT ATC GTT GCT CTG TTC CCG AAT TAT GAT AGT AGA AGA TAT CCA   768
ATT CGA ACA GTT TCC CAA TTA ACA AGA GAA ATT TAT ACA AAC CCA GTA   816
TTA GAA AAT TTT GAT GGT AGT TTT CGA GGC TCG GCT CAG GGC ATA GAA   864
AGA AGT ATT AGG AGT CCA CAT TTG ATG GAT ATA CTT AAC AGT ATA ACC   912
ATC TAT ACG GAT GCT CAT AGG GGT TAT TAT TGG TCA GGG CAT CAA       960
ATA ATG GCT TCT CCT GTA GGG TTT TCG GGG CCA GAA TTC ACT TTT CCG  1008
```

Figure 1-3

```
CTA TAT GGA ACT ATG GGA AAT GCA GCT CCA CAA CAA CGT ATT GTT GCT   1056
CAA CTA GGT CAG GGC GTG TAT AGA ACA TTA TCG TCC ACT TTA TAT AGA   1104
AGA CCT TTT AAT ATA GGG ATA AAT AAT CAA CTA TCT GTT CTT GAC       1152
GGG ACA GAA TTT GCT TAT GGA ACC TCC TCA AAT TTG CCA TCC GCT GTA   1200
TAC AGA AAA AGC GGA ACG GTA GAT TCG CTG GAT GAA ATA CCG CCA CAG   1248
AAT AAC AAC GTG CCA CCT AGG CAA GGA TTT AGT CAT CGA TTA AGC CAT   1296
GTT TCA ATG TTT CGT TCA GGC TTT AGT AAT AGT AGT GTA AGT ATA ATA   1344
AGA GCT CCT ATG TTC TCT TGG ATA CAT CGT AGT GCT GAA TTT AAT AAT   1392
ATA ATT CCT TCA TCA CAA ATT ACA CAA ATA CCT TTA ACA AAA TCT ACT   1440
AAT CTT GGC TCT GGA ACT TCT GTC GTT AAA GGA CCA GGA TTT ACA GGA   1488
```

Figure 1-4

| | | | | | | | | | | | | | | | |
|---|---|---|---|---|---|---|---|---|---|---|---|---|---|---|---|
| GGA | GAT | ATT | CTT | CGA | AGA | ACT | TCA | CCT | GGC | CAG | ATT | TCA | ACC | TTA | AGA | 1536 |
| GTA | AAT | ATT | ACT | GCA | CCA | TTA | TCA | CAA | AGA | TAT | CGG | GTA | AGA | ATT | CGC | 1584 |
| TAC | GCT | TCT | ACC | ACA | AAT | TTA | CAA | TTC | CAT | ACA | TCA | ATT | GAC | GGA | AGA | 1632 |
| CCT | ATT | AAT | CAG | GGG | AAT | TTT | TCA | GCA | ACT | ATG | AGT | AGT | GGG | AGT | AAT | 1680 |
| TTA | CAG | TCC | GGA | AGC | TTT | AGG | ACT | GTA | GGT | TTT | ACT | CCG | TTT | AAC | | 1728 |
| TTT | TCA | AAT | GGA | TCA | AGT | GTA | TTT | ACG | TTA | AGT | GCT | CAT | GTC | TTC | AAT | 1776 |
| TCA | GGC | AAT | GAA | GTT | TAT | ATA | GAT | CGA | ATT | GAA | TTT | GTT | CCG | GCA | GAA | 1824 |
| GTA | ACC | TTT | GAG | GCA | GAA | TAT | GAT | TTA | GAA | AGA | GCA | CAA | AAG | GCG | GTG | 1872 |
| AAT | GAG | CTG | TTT | ACT | TCT | TCC | AAT | CAA | ATC | GGG | TTA | AAA | ACA | GAT | GTG | 1920 |
| ACG | GAT | TAT | CAT | ATT | GAT | CAA | GTA | TCC | AAT | TTA | GTT | GAG | TGT | TTA | TCT | 1968 |

Figure 1-5

```
GAT GAA TTT TGT CTG GAT GAA AAA AAA GAA TTG TCC GAG AAA GTC AAA    2016
CAT GCG AAG CGA CTT AGT GAT GAG CGG AAT TTA CTT CAA GAT CCA AAC    2064
TTT AGA GGG ATC AAT AGA CAA CTA GAC CGT GGC TGG AGA GGA AGT ACG    2112
GAT ATT ACC ATC CAA GGA GGC GAT GAC GTA TTC AAA GAG AAT TAC GTT    2160
ACG CTA TTG GGT ACC TTT GAT GAG TGC TAT CCA ACG TAT TTA TAT CAA    2208
AAA ATA GAT GAG TCG AAA TTA AAA GCC TAT ACC CGT TAC CAA TTA AGA    2256
GGG TAT ATC GAA GAT AGT CAA GAC TTA GAA ATC TAT TTA ATT CGC TAC    2304
AAT GCC AAA CAC GAA ACA GTA AAT GTG CCA GGT ACG GGT TCC TTA TGG    2352
CCG CTT TCA GCC CCA AGT CCA ATC GGA AAA TGT GCC CAT CAT TCC CAT    2400
CAT TTC TCC TTG GAC ATT GAT GTT GGA TGT ACA GAC TTA AAT GAG GAC    2448
TTA GGT GTA TGG GTG ATA TTC AAG ATT AAG ACG CAA GAT GGC CAT GCA    2496
```

Figure 1-6

```
AGA CTA GGA AAT CTA GAA TTT CTC GAA GAG AAA CCA TTA GTA GGA GAA    2544
GCA CTA GCT CGT GTG AAA AGA GCG GAG AAA AAA TGG AGA GAC AAA CGT    2592
GAA AAA TTG GAA TGG GAA ACA AAT ATT GTT TAT AAA GAG GCA AAA GAA    2640
TCT GTA GAT GCT TTA TTT GTA AAC TCT CAA TAT GAT AGA TTA CAA GCG    2688
GAT ACC AAC ATC GCG ATG ATT CAT GCG GCA GAT AAA CGC GTT CAT AGC    2736
ATT CGA GAA GCT TAT CTG CCT GAG CTG TCT GTG ATT CCG GGT GTC AAT    2784
GCG GCT ATT TTT GAA GAA TTA GAA GGG CGT ATT TTC ACT GCA TTC TCC    2832
CTA TAT GAT GCG AGA AAT GTC ATT AAA AAT GGT GAT TTT AAT AAT GGC    2880
TTA TCC TGC TGG AAC GTG AAA GGG CAT GTA GAT GTA GAA GAA CAA AAC    2928
AAC CAC CGT TCG GTC CTT GTT CCG GAA TGG GAA GCA GAA GTG TCA        2976
CAA GAA GTT CGT GTC TGT CCG GGT CGT GGC TAT ATC CTT CGT GTC ACA    3024
```

Figure 1-7

```
GCG TAC AAG GAG GGA TAT GGA GAA GGT TGC GTA ACC ATT CAT GAG ATC   3072
GAG AAC AAT ACA GAC GAA CTG AAG TTT AGC AAC TGT GTA GAA GAG GAA   3120
GTA TAT CCA AAC ACG GTA ACG TAC ACT TCT AAT GAT TAT ACT GCG CAA   3168
GAA GAA TAT GAG GGT ACG TAC ACT TCT CGT AAT CGA GGA TAT GAC GGA   3216
GCC TAT GAA AGC AAT TCT GTA CCA GCT GAT TAT GCA TCA GCC TAT       3264
GAA GAA AAA GCA TAT ACA GAT GGA CGA AGA GAC AAT CCT TGT GAA TCT   3312
AAC AGA GGA TAT GGG GAT TAC ACA CCA GCT CCA GGC TAT GTG ACA       3360
AAA GAA TTA GAG TAC TTC CCA GAA ACC GAT AAG GTA TGG ATT GAG ATC   3408
GGA GAA ACG GAA GGA ACA TTC ATC GTG GAC AGC GTG GAA TTA CTT CTT   3456
ATG GAG GAA                                                       3465
```

Figure 2-1

| | | | | | | | | | | | | | |
|---|---|---|---|---|---|---|---|---|---|---|---|---|---|
| Met<br>1 | Asp | Asn | Pro | Asn | Ile | Asn | Glu | Cys | Ile<br>10 | Pro | Tyr | Asn | Cys<br>15 | Leu |
| Ser | Asn | Pro | Glu<br>20 | Val | Glu | Val | Leu | Gly<br>25 | Gly | Glu | Arg | Ile<br>30 | Thr | Gly |
| Tyr | Thr | Pro<br>35 | Ile | Asp | Ile | Ser | Leu<br>40 | Ser | Leu | Thr | Gln | Phe<br>45 | Leu | Leu Ser |
| Glu | Phe<br>50 | Val | Pro | Gly | Ala | Gly<br>55 | Phe | Val | Leu | Gly | Leu<br>60 | Val | Asp | Ile Ile |
| Trp<br>65 | Gly | Ile | Phe | Gly | Pro<br>70 | Ser | Gln | Trp | Asp | Ala<br>75 | Phe | Leu | Val | Gln Ile<br>80 |
| Glu | Gln | Leu | Ile | Asn<br>85 | Gln | Arg | Ile | Glu | Gly<br>90 | Phe | Ala | Arg | Asn<br>95 | Gln Ala |
| Ile | Ser | Arg | Leu<br>100 | Glu | Gly | Leu | Ser | Asn<br>105 | Leu | Tyr | Gln | Ile<br>110 | Tyr | Ala Glu |

Figure 2-2

| | | | | | | | | | | | | | | | |
|---|---|---|---|---|---|---|---|---|---|---|---|---|---|---|---|
| Ser | Phe | Arg | Glu | Trp | Glu | Ala | Asp | Pro | Thr | Asn | Pro | Ala | Leu | Arg | Glu |
| | | 115 | | | | | 120 | | | | | 125 | | | |
| Glu | Met | Arg | Ile | Gln | Phe | Asn | Asp | Met | Asn | Ser | Ala | Leu | Thr | Thr | Ala |
| | 130 | | | | | 135 | | | | | 140 | | | | |
| Ile | Pro | Leu | Phe | Ala | Val | Gln | Asn | Tyr | Gln | Val | Pro | Leu | Leu | Ser | Val |
| 145 | | | | | 150 | | | | | 155 | | | | | 160 |
| Tyr | Val | Gln | Ala | Ala | Asn | Leu | His | Leu | Ser | Val | Leu | Arg | Asp | Val | Ser |
| | | | | 165 | | | | | 170 | | | | | 175 | |
| Val | Phe | Gly | Gln | Arg | Trp | Gly | Phe | Asp | Ala | Ala | Thr | Ile | Asn | Ser | Arg |
| | | | 180 | | | | | 185 | | | | | 190 | | |
| Tyr | Asn | Asp | Leu | Thr | Arg | Leu | Ile | Gly | Asn | Tyr | Thr | Asp | Tyr | Ala | Val |
| | | 195 | | | | | 200 | | | | | 205 | | | |
| Arg | Trp | Tyr | Asn | Thr | Gly | Leu | Glu | Arg | Val | Trp | Gly | Pro | Asp | Ser | Arg |
| | 210 | | | | | 215 | | | | | 220 | | | | |

Figure 2-3

```
Asp Trp Val Arg Tyr Asn Gln Phe Arg Arg Glu Leu Thr Leu Val
225             230             235             240
Leu Asp Ile Val Ala Leu Phe Pro Asn Tyr Asp Ser Arg Arg Tyr Pro
            245             250             255
Ile Arg Thr Val Ser Gln Leu Thr Arg Glu Ile Tyr Thr Asn Pro Val
        260             265             270
Leu Glu Asn Phe Asp Gly Ser Phe Arg Gly Ser Ala Gln Gly Ile Glu
            275             280             285
Arg Ser Ile Arg Ser Pro His Leu Met Asp Ile Leu Asn Ser Ile Thr
        290             295             300
Ile Tyr Thr Asp Ala His Arg Gly Tyr Tyr Tyr Trp Ser Gly His Gln
        305             310             315             320
Ile Met Ala Ser Pro Val Gly Phe Ser Gly Pro Glu Phe Thr Phe Pro
            325             330             335
```

Figure 2-4

Leu Tyr Gly Thr Met Gly Asn Ala Ala Pro Gln Gln Arg Ile Val Ala
340 345 350

Gln Leu Gly Gln Gly Val Tyr Arg Thr Leu Ser Ser Thr Leu Tyr Arg
355 360 365

Arg Pro Phe Asn Ile Gly Ile Asn Asn Gln Gln Leu Ser Val Leu Asp
370 375 380

Gly Thr Glu Phe Ala Tyr Gly Thr Ser Ser Asn Leu Pro Ser Ala Val
385 390 395 400

Tyr Arg Lys Ser Gly Thr Val Asp Ser Leu Asp Glu Ile Pro Pro Gln
405 410 415

Asn Asn Val Pro Pro Arg Gln Gly Phe Ser His Arg Leu Ser His
420 425 430

Val Ser Met Phe Arg Ser Gly Phe Ser Asn Ser Ser Val Ser Ile Ile
435 440 445

Figure 2-5

| Arg | Ala 450 | Pro | Met | Phe | Ser | Trp 455 | Ile | His | Arg | Ser | Ala 460 | Glu | Phe | Asn | Asn |
| Ile 465 | Ile | Pro | Ser | Ser | Gln 470 | Ile | Thr | Gln | Ile | Pro 475 | Leu | Thr | Lys | Ser | Thr 480 |
| Asn | Leu | Gly | Ser | Gly 485 | Thr | Ser | Val | Val | Lys 490 | Gly | Pro | Gly | Phe | Thr 495 | Gly |
| Gly | Asp | Ile | Leu 500 | Arg | Arg | Thr | Ser | Pro 505 | Gly | Gln | Ile | Ser | Thr 510 | Leu | Arg |
| Val | Asn | Ile 515 | Thr | Ala | Pro | Leu | Ser 520 | Gln | Arg | Tyr | Arg | Val 525 | Arg | Ile | Arg |
| Tyr | Ala 530 | Ser | Thr | Thr | Asn | Leu 535 | Gln | Phe | His | Thr | Ser 540 | Ile | Asp | Gly | Arg |
| Pro 545 | Ile | Asn | Gln | Gly | Asn 550 | Phe | Ser | Ala | Thr | Met 555 | Ser | Ser | Gly | Ser | Asn 560 |

Figure 2-6

Leu Gln Ser Gly Ser Phe Arg Thr Val Gly Phe Thr Thr Pro Phe Asn
                    565             570             575
Phe Ser Asn Gly Ser Ser Val Phe Thr Leu Ser Ala His Val Phe Asn
            580             585             590
Ser Gly Asn Glu Val Tyr Ile Asp Arg Ile Glu Phe Val Pro Ala Glu
            595             600             605
Val Thr Phe Glu Ala Glu Tyr Asp Leu Glu Arg Ala Gln Lys Ala Val
    610             615             620
Asn Glu Leu Phe Thr Ser Ser Asn Gln Ile Gly Leu Lys Thr Asp Val
625             630             635             640
Thr Asp Tyr His Ile Asp Gln Val Ser Asn Leu Val Glu Cys Leu Ser
            645             650             655
Asp Glu Phe Cys Leu Asp Glu Lys Lys Glu Leu Ser Glu Lys Val Lys
            660             665             670

Figure 2-i

His Ala Lys Arg Leu Ser Asp Glu Arg Asn Leu Leu Gln Asp Pro Asn
        675                 680                 685
Phe Arg Gly Ile Asn Arg Gln Leu Asp Arg Gly Trp Arg Gly Ser Thr
        690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
        740                 745                 750
Gly Tyr Ile Glu Asp Ser Gln Asp Leu Glu Ile Tyr Leu Ile Arg Tyr
        755                 760                 765
Asn Ala Lys His Glu Thr Val Asn Val Pro Gly Thr Gly Ser Leu Trp
770                 775                 780

Figure 2-8

Pro Leu Ser Ala Pro Ser Pro Ile Gly Lys Cys Ala His His Ser His
785                 790             795                 800

His Phe Ser Leu Asp Ile Asp Val Gly Cys Thr Asp Leu Asn Glu Asp
            805                 810                 815

Leu Gly Val Trp Val Ile Phe Lys Ile Lys Thr Gln Asp Gly His Ala
        820                 825                 830

Arg Leu Gly Asn Leu Glu Phe Leu Glu Glu Lys Pro Leu Val Gly Glu
        835                 840             845

Ala Leu Ala Arg Val Lys Arg Ala Glu Lys Lys Trp Arg Asp Lys Arg
    850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
            885                 890                 895

Figure 2-9

Asp Thr Asn Ile Ala Met Ile His Ala Ala Asp Lys Arg Val His Ser
              900             905             910
Ile Arg Glu Ala Tyr Leu Pro Glu Leu Ser Val Ile Pro Gly Val Asn
              915             920             925
Ala Ala Ile Phe Glu Glu Gly Leu Glu Gly Arg Ile Phe Thr Ala Phe Ser
              930             935             940
Leu Tyr Asp Ala Arg Asn Val Ile Lys Asn Gly Asp Phe Asn Asn Gly
945           950             955             960
Leu Ser Cys Trp Asn Val Lys Gly His Val Asp Val Glu Gln Asn
              965             970             975
Asn His Arg Ser Val Leu Val Val Pro Glu Trp Glu Ala Glu Val Ser
              980             985             990
Gln Glu Val Arg Val Cys Pro Gly Arg Gly Tyr Ile Leu Arg Val Thr
      995             1000            1005

Figure 2-10

```
Ala Tyr Lys Glu Gly Tyr Gly Glu Gly Cys Val Thr Ile His Glu Ile
        1010            1015            1020
Glu Asn Asn Thr Asp Glu Leu Lys Phe Ser Asn Cys Val Glu Gln Gln
    1025            1030            1035            1040
Val Tyr Pro Asn Asn Thr Val Thr Cys Asn Asp Tyr Thr Ala Thr Gln
                1045            1050            1055
Glu Glu Tyr Glu Gly Thr Tyr Thr Ser Arg Asn Arg Gly Tyr Asp Gly
        1060            1065            1070
Ala Tyr Glu Ser Asn Ser Ser Val Pro Ala Asp Tyr Ala Ser Ala Tyr
        1075            1080            1085
Glu Glu Lys Ala Tyr Thr Asp Gly Arg Arg Asp Asn Pro Cys Glu Ser
        1090            1095            1100
Asn Arg Gly Tyr Gly Asp Tyr Thr Pro Leu Pro Ala Gly Tyr Val Thr
1105            1110            1115            1120
Lys Glu Leu Glu Tyr Phe Pro Glu Thr Asp Lys Val Trp Ile Glu Ile
            1125            1130            1135
Gly Glu Thr Glu Gly Thr Phe Ile Val Asp Ser Val Glu Leu Leu Leu
            1140            1145            1150
Met Glu Glu
        1155
```

Figure 3-1

```
ATG AAC AAT CCG AAC ATC AAT GAA TGC ATT CCT TAT AAT TGT TTA      48
Met Asn Asn Pro Asn Ile Asn Glu Cys Ile Pro Tyr Asn Cys Leu
 1           5               10              15

AGT AAC CCT GAA GTA GAA ATA TTA GGT GGA ATA GAA AGA ATA GAA ACT GGT    96
Ser Asn Pro Glu Val Glu Ile Leu Gly Gly Ile Glu Arg Ile Glu Thr Gly
                  20              25              30

TAC ACC CCA ATC GAT ATT TCC TTG CTA ACG CAA TTT CTT TTG AGT           144
Tyr Thr Pro Ile Asp Ile Ser Leu Leu Thr Gln Phe Leu Leu Ser
             35              40              45

GAA TTT GTT CCC GGT GCT GGA TTT GTG TTA GGA CTA GTT GAT ATA ATA       192
Glu Phe Val Pro Gly Ala Gly Phe Val Leu Gly Leu Val Asp Ile Ile
         50              55              60

TGG GGA ATT TTT GGT CCC TCT CAA TGG GAC GCA TTC TTT GTA CAA ATT       240
Trp Gly Ile Phe Gly Pro Ser Gln Trp Asp Ala Phe Phe Val Gln Ile
 65              70              75              80

GAA CAG TTA ATT AAC AGA ATA GAA GAA GCT AGG AAC CAA GCA               288
Glu Gln Leu Ile Asn Arg Ile Glu Glu Ala Arg Asn Gln Ala
             85              90              95

ATT TCT AGA TTA GAA GGA CTA AGC AAT CTT TAT CAA ATT TAC GCA GAA       336
Ile Ser Arg Leu Glu Gly Leu Ser Asn Leu Tyr Gln Ile Tyr Ala Glu
        100             105             110

TCT TTT AGA GAG TGG GAA GCA GAT CCT ACT AAT CCA GCA TTA AGA GAA       384
Ser Phe Arg Glu Trp Glu Ala Asp Pro Thr Asn Pro Ala Leu Arg Glu
        115             120             125
```

Figure 3-2

| | | | | | | | | | | |
|---|---|---|---|---|---|---|---|---|---|---|
| GAG | ATG | CGT | ATT | CAA | TTC | AAT | GAC | ATG | AAC | AGT | GCC | CTT | ACA | ACC | GCT | 432 |
| Glu | Met | Arg | Ile | Gln | Phe | Asn | Asp | Met | Asn | Ser | Ala | Leu | Thr | Thr | Ala | |
| | 130 | | | | | 135 | | | | 140 | | | | | | |
| ATT | CCT | CTT | TTT | GCA | GTT | CAA | AAT | TAT | CAA | AGT | CCT | CTT | TTA | TCA | GTA | 480 |
| Ile | Pro | Leu | Phe | Ala | Val | Gln | Asn | Tyr | Gln | Val | Pro | Leu | Leu | Ser | Val | |
| 145 | | | | | 150 | | | | | 155 | | | | | 160 | |
| TAT | GTT | CAA | GCT | GCA | AAT | TTA | CAT | TTA | TCA | GTT | TTG | AGA | GAT | GTT | TCA | 528 |
| Tyr | Val | Gln | Ala | Ala | Asn | Leu | His | Leu | Ser | Val | Leu | Arg | Asp | Val | Ser | |
| | | | 165 | | | | | 170 | | | | | | 175 | | |
| GTG | TTT | GGA | CAA | TGG | GGA | TTT | GAT | GCC | GCG | ACT | ATC | AAT | AGT | CGT | | 576 |
| Val | Phe | Gly | Gln | Trp | Gly | Phe | Asp | Ala | Ala | Thr | Ile | Asn | Ser | Arg | | |
| | | 180 | | | | | 185 | | | | | 190 | | | | |
| TAT | AAT | GAT | TTA | ACT | AGG | CTT | ATT | GGC | TAT | ACA | GAT | TAT | GCT | GTA | | 624 |
| Tyr | Asn | Asp | Leu | Thr | Arg | Leu | Ile | Gly | Tyr | Thr | Asp | Tyr | Ala | Val | | |
| | | 195 | | | | | 200 | | | | | 205 | | | | |
| CGC | TGG | TAC | AAT | ACG | GGA | CTT | GAA | CGT | GTA | TGG | GGA | CCG | GAT | TCT | AGA | 672 |
| Arg | Trp | Tyr | Asn | Thr | Gly | Leu | Glu | Arg | Val | Trp | Gly | Pro | Asp | Ser | Arg | |
| 210 | | | | | 215 | | | | | 220 | | | | | | |
| GAT | TGG | GTA | AGG | TAT | AAT | CAA | TTT | AGA | AGA | GAA | TTA | ACA | CTA | ACT | GTA | 720 |
| Asp | Trp | Val | Arg | Tyr | Asn | Gln | Phe | Arg | Arg | Glu | Leu | Thr | Leu | Thr | Val | |
| 225 | | | | | 230 | | | | | 235 | | | | | 240 | |
| TTA | GAT | ATC | GTT | GCT | CTG | TTC | CCG | AAT | TAT | GAT | AGT | AGA | AGA | TAT | CCA | 768 |
| Leu | Asp | Ile | Val | Ala | Leu | Phe | Pro | Asn | Tyr | Asp | Ser | Arg | Arg | Tyr | Pro | |
| | | | 245 | | | | | 250 | | | | | | 255 | | |

Figure 3-3

```
ATT CGA ACA GTT TCC CAA TTA ACA AGA GAA ATT TAT ACA AAC CCA GTA      816
Ile Arg Thr Val Ser Gln Leu Thr Arg Glu Ile Tyr Thr Asn Pro Val
            260                 265                 270

TTA GAA AAT TTT GAT GGT AGT TTT CGA GGC TCG GCT CAG GGC ATA GAA      864
Leu Glu Asn Phe Asp Gly Ser Phe Arg Gly Ser Ala Gln Gly Ile Glu
        275                 280                 285

AGA AGT ATT AGG AGT CCA CAT TTG ATG GAT ATA CTT TAT ACA AGT ATA ACC 912
Arg Ser Ile Arg Ser Pro His Leu Met Asp Ile Leu Tyr Thr Ser Ile Thr
    290                 295                 300

ATC TAT ACG GAT GCT CAT AGG GGT TAT TAT TAT TGG TCA GGG CAT CAA      960
Ile Tyr Thr Asp Ala His Arg Gly Tyr Tyr Tyr Trp Ser Gly His Gln
305                 310                 315                 320

ATA ATG GCT TCT CCT GTA GGG TTT TCG GGG CCA GAA TTC ACT TTT CCG     1008
Ile Met Ala Ser Pro Val Gly Phe Ser Gly Pro Glu Phe Thr Phe Pro
                325                 330                 335

CTA TAT GGA AAT GCA GCT ATG GGA AAT GCA CCA CAA CAA CGT ATT GTT GCT 1056
Leu Tyr Gly Asn Ala Ala Met Gly Asn Ala Pro Gln Gln Arg Ile Val Ala
340                 345                 350
```

Figure 3-4

```
CAA CTA GGT CAG GGC GTG TAT AGA ACA TTA TCG TCC ACT TTA TAT AGA     1104
Gln Leu Gly Gln Gly Val Tyr Arg Thr Leu Ser Ser Thr Leu Tyr Arg
        355             360             365

AGA CCT TTT AAT ATA GGG ATA AAT CAA CAA CTA TCT GTT CTT GAC         1152
Arg Pro Phe Asn Ile Gly Ile Asn Gln Gln Leu Ser Val Leu Asp
    370             375             380

GGG ACA GAA TTT GCT TAT GGA ACC TCC TCA AAT TTG CCA TCT GCT GTA     1200
Gly Thr Glu Phe Ala Tyr Gly Thr Ser Ser Asn Leu Pro Ser Ala Val
385             390             395             400

TAC AGA AAA AGC GGA ACG GTA GAT TCG CTG GAT GAA ATA CCG CCA CAG     1248
Tyr Arg Lys Ser Gly Thr Val Asp Ser Leu Asp Glu Ile Pro Pro Gln
            405             410             415

AAT AAC AAC GTG CCA CCT AGG CAA GGA TTT AGT CAT CGA TTA AGC CAT     1296
Asn Asn Asn Val Pro Pro Arg Gln Gly Phe Ser His Arg Leu Ser His
                420             425             430
```

Figure 3-5

| | | | | | | | | | | | | | | | | |
|---|---|---|---|---|---|---|---|---|---|---|---|---|---|---|---|---|
| GTT Val | TCA Ser 435 | ATG Met | TTT Phe | CGT Arg | TCA Ser | GGC Gly 440 | TTT Phe | AGT Ser | AAT Asn | AGT Ser | AGT Ser 445 | GTA Val | ATA Ile | ATA Ile | | 1344 |
| AGA Arg | GCT Ala 450 | CCT Pro | ATG Met | TTC Phe | TCT Ser | TGG Trp 455 | ATA Ile | CAT His | CGT Arg | AGT Ser | GCT Ala 460 | GAA Glu | TTT Phe | AAT Asn | AAT Asn | 1392 |
| ATA Ile | ATT Ile 465 | CCT Pro | TCA Ser | CAA Gln | TCA Ser 470 | CAA Gln | ATT Ile | ACA Thr | ATA Ile | CCT Pro 475 | TTA Leu | ACA Thr | AAA Lys | TCT Ser | ACT Thr 480 | 1440 |
| AAT Asn | CTT Leu | GGC Gly 485 | TCT Ser | GGA Gly | ACT Thr | TCT Ser | GTC Val | GTT Val 490 | AAA Lys | GGA Gly | CCA Pro | GGA Gly | TTT Phe | ACA Thr 495 | GGA Gly | 1488 |
| GGA Gly | GAT Asp | ATT Ile | CTT Leu 500 | CGA Arg | AGA Arg | ACT Thr | CCT Pro 505 | GGC Gln | CAG Gln | ATT Ile | TCA Ser | ACC Thr 510 | TTA Leu | AGA Arg | | 1536 |

Figure 3-6

| | | | | | | | | | | | | | | | |
|---|---|---|---|---|---|---|---|---|---|---|---|---|---|---|---|
| GTA<br>Val | AAT<br>Asn | ATT<br>Ile<br>515 | ACT<br>Thr | GCA<br>Ala | CCA<br>Pro | TTA<br>Leu | TCA<br>Ser<br>520 | CAA<br>Gln | AGA<br>Arg | TAT<br>Tyr | CGG<br>Arg | GTA<br>Val<br>525 | AGA<br>Arg | ATT<br>Ile | CGC<br>Arg | 1584 |
| TAC<br>Tyr | GCT<br>Ala<br>530 | TCT<br>Ser | ACC<br>Thr | ACA<br>Thr | AAT<br>Asn | TTA<br>Leu<br>535 | CAA<br>Gln | TTC<br>Phe | CAT<br>His | ACA<br>Thr | TCA<br>Ser<br>540 | ATT<br>Ile | GAC<br>Asp | GGA<br>Gly | AGA<br>Arg | 1632 |
| CCT<br>Pro<br>545 | ATT<br>Ile | AAT<br>Asn | CAG<br>Gln | GGG<br>Gly | AAT<br>Asn<br>550 | CAA<br>Gln | TTT<br>Phe | TCA<br>Ser | GCA<br>Ala | ACT<br>Thr<br>555 | ATG<br>Met | AGT<br>Ser | AGT<br>Ser | GGG<br>Gly | AGT<br>Ser<br>560 | AAT<br>Asn | 1680 |
| TTA<br>Leu | CAG<br>Gln | TCC<br>Ser | GGA<br>Gly<br>565 | AGC<br>Ser | TTT<br>Phe | AGG<br>Arg | ACT<br>Thr | GTA<br>Val<br>570 | GGT<br>Gly | TTT<br>Phe | ACT<br>Thr | CCG<br>Pro | TTT<br>Phe<br>575 | AAC<br>Asn | | 1728 |
| TTT<br>Phe | TCA<br>Ser | AAT<br>Asn<br>580 | GGA<br>Gly | TCA<br>Ser | AGT<br>Ser | GTA<br>Val | TTT<br>Phe<br>585 | ACG<br>Thr | TTA<br>Leu | AGT<br>Ser | GCT<br>Ala | CAT<br>His<br>590 | GTC<br>Val | TTC<br>Phe | AAT<br>Asn | 1776 |
| TCA<br>Ser | GGC<br>Gly<br>595 | AAT<br>Asn | GAA<br>Glu | GTT<br>Val | TAT<br>Tyr | ATA<br>Ile | GAT<br>Asp<br>600 | CGA<br>Arg | ATT<br>Ile | GAA<br>Glu | TTT<br>Phe | GTT<br>Val<br>605 | CCG<br>Pro | GCA<br>Ala | GAA<br>Glu | 1824 |

Figure 3-7

| | | | | | | | | | | | | | | | | |
|---|---|---|---|---|---|---|---|---|---|---|---|---|---|---|---|---|
| GTA<br>Val<br>610 | ACC<br>Thr | TTT<br>Phe | GAG<br>Glu | GCA<br>Ala | GAA<br>Glu | TAT<br>Tyr<br>615 | GAT<br>Asp | TTA<br>Leu | GAA<br>Glu | AGA<br>Arg | GCA<br>Ala<br>620 | CAA<br>Gln | AAG<br>Lys | GCG<br>Ala | GTG<br>Val | 1872 |
| AAT<br>Asn<br>625 | GAG<br>Glu | CTG<br>Leu | TTT<br>Phe | ACT<br>Thr | TCT<br>Ser<br>630 | TCC<br>Ser | AAT<br>Asn | CAA<br>Gln | ATC<br>Ile | GGG<br>Gly<br>635 | TTA<br>Leu | AAA<br>Lys | ACA<br>Thr | GAT<br>Asp | GTG<br>Val<br>640 | 1920 |
| ACG<br>Thr | GAT<br>Asp | TAT<br>Tyr | CAT<br>His<br>645 | ATT<br>Ile | GAT<br>Asp | CAA<br>Gln | GTA<br>Val | TCC<br>Ser<br>650 | AAT<br>Asn | TTA<br>Leu | GTT<br>Val | GAG<br>Glu | TGT<br>Cys | TTA<br>Leu<br>655 | TCT<br>Ser | 1968 |
| GAT<br>Asp | GAA<br>Glu | TTT<br>Phe | TGT<br>Cys<br>660 | CTG<br>Leu | GAT<br>Asp | GAA<br>Glu | TCC<br>Ser | AAA<br>Lys<br>665 | AAA<br>Lys | GAA<br>Glu | TTG<br>Leu | TCC<br>Ser | GAG<br>Glu | AAA<br>Lys<br>670 | GTC<br>Val | 2016 |
| CAT<br>His | GCG<br>Ala | CGA<br>Arg<br>675 | AAG<br>Lys | CTT<br>Leu | AGT<br>Ser | GAT<br>Asp | GAG<br>Glu<br>680 | CGG<br>Arg | AAT<br>Asn | TTA<br>Leu | CTT<br>Leu | CAA<br>Gln<br>685 | GAT<br>Asp | CCA<br>Pro | AAC<br>Asn | 2064 |

Figure 3-8

| | | | | | | | | | | | | | | | |
|---|---|---|---|---|---|---|---|---|---|---|---|---|---|---|---|
|TTT|AGA|GGG|ATC|AAT|AGA|CAA|CTA|GAC|CGT|GGC|TGG|AGA|GGA|AGT|ACG|
|Phe|Arg|Gly|Ile|Asn|Arg|Gln|Leu|Asp|Arg|Gly|Trp|Arg|Gly|Ser|Thr|
| |690| | | |695| | | | |700| | | | | |

2112

|GAT|ATT|ACC|ATC|CAA|GGA|GGC|GAT|GAC|GTA|TTC|AAA|GAG|AAT|TAC|GTT|
|---|---|---|---|---|---|---|---|---|---|---|---|---|---|---|---|
|Asp|Ile|Thr|Ile|Gln|Gly|Gly|Asp|Asp|Val|Phe|Lys|Glu|Asn|Tyr|Val|
|705| | | | |710| | | | |715| | | | |720|

2160

|ACG|CTA|TTG|GGT|ACC|TTT|GAT|GAG|TGC|TAT|CCA|ACG|TAT|TTA|TAT|CAA|
|---|---|---|---|---|---|---|---|---|---|---|---|---|---|---|---|
|Thr|Leu|Leu|Gly|Thr|Phe|Asp|Glu|Cys|Tyr|Pro|Thr|Tyr|Leu|Tyr|Gln|
| | | | |725| | | | |730| | | | |735| |

2208

|AAA|ATA|GAT|GAG|TCG|AAA|TTA|AAA|GCC|TAT|ACC|CGT|TAC|CAA|TTA|AGA|
|---|---|---|---|---|---|---|---|---|---|---|---|---|---|---|---|
|Lys|Ile|Asp|Glu|Ser|Lys|Leu|Lys|Ala|Tyr|Thr|Arg|Tyr|Gln|Leu|Arg|
| | | |740| | | | |745| | | | |750| | |

2256

|GGG|TAT|ATC|GAA|GAT|AGT|CAA|GAC|TTA|GAA|ATC|TAT|TTA|ATT|CGC|TAC|
|---|---|---|---|---|---|---|---|---|---|---|---|---|---|---|---|
|Gly|Tyr|Ile|Glu|Asp|Ser|Gln|Asp|Leu|Glu|Ile|Tyr|Leu|Ile|Arg|Tyr|
| |755| | | | |760| | | | |765| | | | |

| | | | | | | | | | |
|---|---|---|---|---|---|---|---|---|---|
| AAT Asn | GCC Ala 770 | AAA Lys | CAC His | GAA Glu | ACA Thr | GTA Val 775 | AAT Asn | GTG Val | CCA Pro | GGT Gly | ACG Thr 780 | GGT Gly | TCC Ser | TTA Leu | TGG Trp | 2352 |
| CCG Pro 785 | CTT Leu | TCA Ser | GCC Ala | CCA Pro | AGT Ser 790 | CCA Pro | ATC Ile | GGA Gly | AAA Lys | TGT Cys 795 | GCC Ala | CAT His | TCC Ser | CAT His 800 | | 2400 |
| CAT His | TTC Phe | TCC Ser | TTG Leu | GAC Asp 805 | ATT Ile | GAT Asp | GTT Val | GGA Gly | TGT Cys 810 | ACA Thr | GAC Asp | TTA Leu | AAT Asn | GAG Glu 815 | GAC Asp | 2448 |
| TTA Leu | GGT Gly | GTA Val | TGG Trp 820 | GTG Val | ATA Ile | TTC Phe | AAG Lys 825 | ATT Ile | AAG Lys | ACG Thr | CAA Gln | GAT Asp | GGC Gly 830 | CAT His | GCA Ala | 2496 |
| AGA Arg | CTA Leu 835 | GGA Gly | AAT Asn | CTA Leu | GAA Glu | TTT Phe 840 | CTC Leu | GAA Glu | GAG Glu | AAA Lys | CCA Pro 845 | TTA Leu | GTA Val | GGA Gly | GAA Glu | 2544 |
| GCA Ala | CTA Leu 850 | GCT Ala | CGT Arg | GTG Val | AAA Lys | AGA Arg 855 | GCG Ala | GAG Glu | AAA Lys | AAA Lys | TGG Trp 860 | AGA Arg | GAC Asp | AAA Lys | CGT Arg | 2592 |

Figure 3-10

| | | | | | | | | | | | | | | | |
|---|---|---|---|---|---|---|---|---|---|---|---|---|---|---|---|
| GAA Glu 865 | AAA Lys | TTG Leu | GAA Glu | TGG Trp 870 | GAA Glu | ACA Thr | AAT Asn | ATT Ile | GTT Val 875 | TAT Tyr | AAA Lys | GAG Glu | GCA Ala | AAA Lys | GAA Glu 880 | 2640 |
| TCT Ser | GTA Val | GAT Asp | GCT Ala | TTA Leu 885 | TTT Phe | GTA Val | AAC Asn | TCT Ser | CAA Gln 890 | TAT Tyr | GAT Asp | AGA Arg | TTA Leu | CAA Gln 895 | GCG Ala | 2688 |
| GAT Asp | ACC Thr | AAC Asn | ATC Ile | GCG Ala 900 | ATG Met | ATT Ile | CAT His | GCG Ala | GCA Ala 905 | GAT Asp | AAA Lys | CGC Arg | GTT Val 910 | CAT His | AGC Ser | 2736 |
| ATT Ile | CGA Arg | GAA Glu | GCT Ala | TAT Tyr 915 | CTG Leu | CCT Pro | GAG Glu 920 | CTG Leu | TCT Ser | GTG Val | ATT Ile | CCG Pro 925 | GGT Gly | GTC Val | AAT Asn | 2784 |
| GCG Ala | GCT Ala 930 | ATT Ile | TTT Phe | GAA Glu | GAA Glu | TTA Leu 935 | GAA Glu | GGG Gly | CGT Arg | ATT Ile | TTC Phe 940 | GCA Ala | ACT Thr | TTC Phe | TCC Ser | 2832 |

Figure 3-11

```
CTA TAT GAT GCG AGA AAT GTC ATT AAA AAT GGT GAT TTT AAT GGC           2880
Leu Tyr Asp Ala Arg Asn Val Ile Lys Asn Gly Asp Phe Asn Gly
945                     950                 955                 960

TTA TCC TGC TGG AAC GTG AAA GGG CAT GTA GAT GTA GAA CAA AAC           2928
Leu Ser Cys Trp Asn Val Lys Gly His Val Asp Val Glu Gln Asn
            965                 970                     975

AAC CAC CGT TCG GTC CTT GTT CCG GGT CAT GAA TGG GAA GCA GTG TCA      2976
Asn His Arg Ser Val Leu Val Pro Gly His Glu Trp Glu Ala Val Ser
                980             985                 990

CAA GAA GTT CGT GTC TGT CCG GGT CGT GGC TAT ATC CTT CGT GTC ACA      3024
Gln Glu Val Arg Val Cys Pro Gly Arg Gly Tyr Ile Leu Arg Val Thr
                995             1000                1005

GCG TAC AAG GAG GGA TAT GGA GAA GGT TGC GTA ACC ATT CAT GAG ATC      3072
Ala Tyr Lys Glu Gly Tyr Gly Glu Gly Cys Val Thr Ile His Glu Ile
1010                1015                    1020
```

Figure 3-12

```
GAG AAC AAT ACA GAC GAA CTG AAG TTT AGC AAC TGT GTA GAA GAG GAA
Glu Asn Asn Thr Asp Glu Leu Lys Phe Ser Asn Cys Val Glu Glu Glu
1025              1030                1035                1040       3120

GTA TAT CCA AAC AAC ACG GTA ACG TGT AAT GAT TAT ACT GCG ACT CAA
Val Tyr Pro Asn Asn Thr Val Thr Cys Asn Asp Tyr Thr Ala Thr Gln
                1045                1050                1055         3168

GAA TAT GAG GGT ACG TAC TAC ACT TCT CGT AAT CGA GGA TAT GAC GGA
Glu Tyr Glu Gly Thr Tyr Tyr Thr Ser Arg Asn Arg Gly Tyr Asp Gly
                1060                1065                1070         3216

GCC TAT GAA AGC AAT TCT GTA CCA GCT GAT TAT GCA TCA GCC TAT
Ala Tyr Glu Ser Asn Ser Val Pro Ala Asp Tyr Ala Ser Ala Tyr
                1075                1080                1085         3264

GAA AAA GCA TAT ACA GAT GGA CGA AGA GAC AAT CCT TGT GAA TCT
Glu Lys Ala Tyr Thr Asp Gly Arg Arg Asp Asn Pro Cys Glu Ser
                1090                1095                1100         3312
```

Figure 3-13

| AAC | AGA | GGA | TAT | GGG | GAT | TAC | ACA | CCA | CTA | CCA | GCT | GGC | TAT | GTG | ACA | |
|---|---|---|---|---|---|---|---|---|---|---|---|---|---|---|---|---|
| Asn | Arg | Gly | Tyr | Gly | Asp | Tyr | Thr | Pro | Leu | Pro | Ala | Gly | Tyr | Val | Thr | 3360 |
| 1105 | | | | | 1110 | | | 1115 | | | | | | | 1120 | |
| AAA | GAA | TTA | GAG | TAC | TTC | CCA | GAA | ACC | GAT | AAG | GTA | TGG | ATT | GAG | ATC | |
| Lys | Glu | Leu | Glu | Tyr | Phe | Pro | Glu | Thr | Asp | Lys | Val | Trp | Ile | Glu | Ile | 3408 |
| | | | | 1125 | | | | | 1130 | | | | | 1135 | | |
| GGA | GAA | ACG | GAA | GGA | ACA | TTC | ATC | GTG | GAC | AGC | GTG | GAA | TTA | CTT | CTT | |
| Gly | Glu | Thr | Glu | Gly | Thr | Phe | Ile | Val | Asp | Ser | Val | Glu | Leu | Leu | Leu | 3456 |
| | | 1140 | | | | | 1145 | | | | | | 1150 | | | |
| ATG | GAG | GAA | | | | | | | | | | | | | | 3465 |
| Met | Glu | Glu | | | | | | | | | | | | | | |
| | | 1155 | | | | | | | | | | | | | | |

5,055,294

CHIMERIC *BACILLUS THURINGIENSIS* CRYSTAL PROTEIN GENE COMPRISING HD-73 AND BERLINER 1715 TOXIN GENES, TRANSFORMED AND EXPRESSED IN *PSEUDOMONAS FLUORESCENS*

BACKGROUND OF THE INVENTION

The most widely used microbial pesticides are derived from the bacterium *Bacillus thuringiensis*. This bacterial agent is used to control a wide range of leaf-eating caterpillars, Japanese beetles and mosquitoes. *Bacillus thuringiensis* produces a proteinaceous paraspore or crystal which is toxic upon ingestion by a susceptible insect host. For example, *B. thuringiensis* var. kurstaki HD-1 produces a crystal called a delta toxin which is toxic to the larvae of a number of lepidopteran insects. The cloning and expression of this B.t. crystal protein gene in *Escherichia coli* has been described in the published literature (Schnepf, H. E. and Whitely, H. R. [1981] Proc. Natl. Acad. Sci. U.S.A. 78:2893-2897). U.S. Pat. No. 4,448,885 and U.S. Pat. No. 4,467,036 both disclose the expression of B.t. crystal protein in *E. coli*. In U.S. Pat. No. 4,467,036 *B. thuringiensis* var. kurstaki HD-1 is disclosed as being available from the well-known NRRL culture repository at Peoria, Ill. Its accession number there is NRRL B3792. *B. thuringiensis* var. kurstaki HD-73 is also available from NRRL. Its accession number is NRRL B-4488.

BRIEF SUMMARY OF THE INVENTION

Disclosed and claimed is a novel hybrid toxin gene toxic to lepidopteran insects. This toxin gene has been transferred to a *Pseudomonas fluorescens* host via a plasmid vector.

Specifically, the invention comprises a novel hybrid delta endotoxin gene comprising part of the *B. thuringiensis* var. kurstaki strain HD-73 toxin gene and part of the toxin gene from *B. thuringiensis* var. *thuringiensis* strain Berliner 1715 (DNA 5:305-314, 1986). This hybrid gene was inserted into a suitable transfer vector which was then used to transform a *Pseudomonas fluorescens* host. The *P. fluorescens* host can be used as an insecticide active against lepidopteran insects.

More specifically, the subject invention concerns a novel hybrid toxin gene (DNA) encoding a novel protein having activity against lepidopteran insects. FIG. 1 discloses the DNA encoding the novel toxin. FIG. 2 discloses the amino acid sequence of the novel hybrid toxin. FIG. 3 is a composite of FIGS. 1 and 2.

BRIEF DESCRIPTION OF THE DRAWINGS

FIG. 1 (parts 1-7)—DNA encoding the novel toxin.
FIG. 2 (parts 1-10)—Amino acid sequence of the novel toxin.
FIG. 3 (parts 1-13)—A composite of FIG. 1 and FIG. 2.

DETAILED DISCLOSURE OF THE INVENTION

The novel hybrid toxin gene of the subject invention comprises part of the *B. thuringiensis* var. kurstaki strain HD-73 toxin gene and part of a *B. thuringiensis* var. *thuringiensis* strain Berliner 1715 toxin gene. In general, the B.t.k. HD-73 gene portion was initially combined with DNA segments derived from (1) the known *E. coli* plasmid pBR322, and (2) a DNA segment representing the hybrid Tac promoter. Next, the 3' part of the Berliner toxin gene was added followed by a DNA segment conferring the ability to replicate in Pseudomonas from the known plasmid pRO1614.

The resulting hybrid gene was contained in a plasmid named pM3,130-7. This plasmid was used to transform a *Pseudomonas fluorescens* microbe to give the transformed strain named MR420.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSFlOlO, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Construction of Novel Hybrid Toxin Gene and Transformation into *Pseudomonas fluorescens*

A portion of the *B. thuringiensis* var. kurstaki HD-73 gene including all of the toxin-encoding DNA from the starting ATG (i.e., start methionine) to the HindIII site was inserted into the Tac-promoted plasmid pKK223-3 (Pharmacia). This was done by making a blunt fusion of this gene just downstream from the ribosome binding site in pKK223-3. This formed plasmid pKK2. Plasmid pKK2 was completely digested with HindIII which cleaves at the ultimate 3' end of the toxin gene. The HindIII overhang was made blunt by filling it in with deoxynucleotides using Klenow fragment. Next, PstI linker was added to the new blunt site followed by digestion with PstI and closing up of the plasmid with DNA ligase. Then the 3' portion of the Berliner toxin sequence (DNA 5:305-314, 1986) was cloned as a SacI to PstI fragment into the modified pKK2/SacI–PstI thus making a recombinant toxin gene in a new plasmid named pKK73BB-9. This gene is of Berliner origin for all sequences beyond (3' to) the SacI site.

Next, pKK73BB-9 was completely digested with PstI, which cleaves at the ultimate 3' end of the new chimeric toxin gene, and treated with bacterial alkaline phosphatase. The PstI DNA fragment, from plasmid pR01614, which confers the ability to replicate in Pseudomonas was then inserted into the pKK73BB-9/PstI vector to form plasmid pM2,107-1. Plasmid pM2,107-1 was completely digested with the restriction endonuclease TthIIII, the open site overhang was made blunt by treatment with Klenow fragment plus deoxynucleotides, linkered for BamH1, BamH1 digested, ligated, transformed, and screened to find a plasmid which had deleted the useless partial tetracycline resistance gene (derived from pKK223-3). This gave plasmid pM3,123-1. Plasmid pM3,123-1 was cleaved with the restriction endonuclease PvuI, digested very briefly with Bal31, made blunt by treatment with Klenow fragment and deoxynucleoside triphosphates, and used as a vector to clone the similarly blunted tetracycline resistance gene from pBR322 (map positions EcoRI and AvaI). Screening of tetracycline resistant colonies produced the desired plasmid called pM3,130-7. This plasmid was then transformed, using standard procedures, into a *Pseudomonas fluorescens*. The resulting transformed strain is called MR420.

The above cloning procedures were conducted using standard procedures unless otherwise noted.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pM3,130-7, containing the B.t. toxin gene, can be removed from the transformed host microbe by use of standard well-known procedures. For example, *P. fluorescens* (pM3,130-7) can be subjected to cleared lysate isopycnic density gradient procedures, and the like, to recover pM3,130-7.

A subculture of *P. fluorescens* (pM3,130-7) has been deposited in the permanent collection of the Agricultural Research Service Patent Culture Collection (NRRL), Regional Research Center, 1815 North University Street, Peoria, Ill. 61604 U.S.A. on Feb. 22, 1988. The culture was assigned the accession number NRRL B-18332 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing the deposit.

EXAMPLE 2

Insertion of Toxin Gene Into Plants

The novel gene coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983]0 Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 3

Cloning of Novel Hybrid *B. thuringiensis* Genes Into Baculoviruses

The novel hybrid gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel B.t. toxin gene is shown in FIG. 1. The deduced amino acid sequence is shown in FIG. 2.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.
A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequence of the B.t. toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

I claim:

1. DNA encoding a B.t. toxin having the amino acid sequence shown in FIG. 2.

2. DNA, according to claim 1, having the nucleotide sequence shown in FIG. 1.

3. DNA, according to claim 1, having the nucleotide sequence shown in FIG. 1, wherein said sequence terminates at the stop codon.

4. A recombinant DNA transfer vector comprising DNA which codes for the amino acid sequence shown in FIG. 2.

5. The DNA transfer vector, according to claim 4, transferred to and replicated in a prokaryotic or eukaryotic host.

6. A bacterial host transformed to express a B.t. toxin having the amino acid sequence shown in FIG. 2.

7. *Pseudomonas fluorescens*, according to claim 6, transformed with a plasmid vector containing the B.t. toxin gene encoding the B.t. toxin having the amino acid sequence shown in FIG. 2.

8. *Pseudomonas fluorescens* (pM3,130-7), having the identifying characteristic of NRRL B-18332, a *Pseudomonas fluorescens* according to claim 7.

9. A microorganism according to claim 6, which is a species of Pseudomonas, Azotobacter, Erwinia, Serratia, Klebsiella, Rhizobium, Rhodopseudomonas, Methylophilius, Agrobacterium, Acetobacter or Alcaligenes.

10. A microorganism according to claim 9, wherein said microorganism is pigmented and phylloplane adherent.

11. A method for controlling lepidopteran insects which comprises administering to said insects or to the environment of said insects a microorganism according to claim 9.

12. A method according to claim 11, wherein said administration is to the rhizosphere.

13. A method according to claim 12, wherein said administration is to the phylloplane.

14. A method according to claim 11, wherein said administration is to a body of water.

15. An insecticidal composition comprising insecticide containing substantially intact, treated cells having prolonged pesticidal activity when applied to the environment of a target pest, wherein said insecticide is a polypeptide toxic to lepidopteran insects, is intracellular, and is produced as a result of expression of a transformed microbe capable of expressing the B.t. toxin having the amino acid sequence shown in FIG. 2.

16. The insecticidal composition, according to claim 15, wherein said treated cells are treated by chemical or physical means to prolong the insecticidal activity in the environment.

17. The insecticidal composition, according to claim 16, wherein said cells are prokaryotes or lower eukaryotes.

18. The insecticidal composition, according to claim 17, wherein said prokaryote cells are selected from the group consisting of Enterobacteriaceae, Bacillaceae, Rhizobiaceae, Spirillaceae, Lactobacillaceae, Pseudomonadaceae, Azotobacteraceae, and Nitrobacteraceae.

19. The insecticidal composition, according to claim 17, wherein said lower eukaryote cells are selected from the group consisting of Phycomycetes, Ascomycetes, and Basidiomycetes.

20. The insecticidal composition, according to claim 15, wherein said cell is a pigmented bacterium, yeast, or fungus.

21. Treated, substantially intact unicellular microorganism cells containing an intracellular toxin, which toxin is a result of expression of a *Bacillus thuringiensis* toxin gene toxic to lepidopteran insects which codes for a polypeptide toxin having the amino acid sequence shown in FIG. 2, wherein said cells are treated under conditions which prolong the insecticidal activity when said cell is applied to the environment of a target insect.

22. The cells, according to claim 21, wherein the cells are treated by chemical or physical means to prolong the insecticidal activity in the environment.

23. The cells according to claim 21, wherein said microorganism is Pseudomonas and said toxin is a B.t. toxin having the amino acid sequence shown in FIG. 2.

24. Pseudomonas cells according to claim 23, wherein said cells are treated with iodine.

25. The cells, according to claim 21, which are *Pseudomonas fluorescens*.

26. The cells, according to claim 25, which are *Pseudomonas fluorescens* (pM3,130-7).

27. A plasmid selected from the group consisting of pM2,107-1, pM3,123-1 and pM3,130-7.

28. Plasmid pM3,130-7, according to claim 27.

* * * * *

UNITED STATES PATENT AND TRADEMARK OFFICE
CERTIFICATE OF CORRECTION

PATENT NO. : 5,055,294

DATED : October 8, 1991

INVENTOR(S) : Thomas E. Gilroy

It is certified that error appears in the above-identified patent and that said Letters Patent is hereby corrected as shown below:

Column 1  line 27:  "NRRL B3792" should read --NRRL B-3792--.
Column 4  line 36:  "RSFIOIO" should read --RSF1010--.
Column 8  line 33:  "[1983]0Cell" should read --[1983] Cell--.
Column 10 line 6 :  "Klehsiella" should read --Klebsiella--.
(Claim 9)

Signed and Sealed this

Nineteenth Day of January, 1993

Attest:

DOUGLAS B. COMER

Attesting Officer

Acting Commissioner of Patents and Trademarks